US010550062B2

(12) United States Patent
Myllyoja et al.

(10) Patent No.: US 10,550,062 B2
(45) Date of Patent: Feb. 4, 2020

(54) METHOD FOR CATALYTIC CONVERSION OF KETOACIDS AND HYDROTREAMENT TO HYDROCARBONS (71) Applicant: NESTE OYJ, Espoo (FI)

(72) Inventors: Jukka Myllyoja, Vantaa (FI); Rami Piilola, Helsinki (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 15/276,065

(22) Filed: Sep. 26, 2016

(65) Prior Publication Data
US 2017/0073294 A1 Mar. 16, 2017

Related U.S. Application Data (63) Continuation of application No. PCT/FI2015/050208, filed on Mar. 26, 2015.

(30) Foreign Application Priority Data

Mar. 26, 2014 (EP) ..................................... 14161793

(51) Int. Cl.
| | | |
|---|---|---|
| *C07C 51/00* | (2006.01) |
| *C07C 51/353* | (2006.01) |
| *C10G 50/00* | (2006.01) |
| *C10L 1/06* | (2006.01) |
| *C10G 3/00* | (2006.01) |
| *B01J 35/10* | (2006.01) |
| *C10L 1/08* | (2006.01) |
| *B01J 35/00* | (2006.01) |
| *C07C 59/347* | (2006.01) |
| *B01J 23/10* | (2006.01) |
| *B01J 23/30* | (2006.01) |
| *C07C 51/367* | (2006.01) |
| *C07D 307/33* | (2006.01) |
| *B01J 21/04* | (2006.01) |
| *B01J 21/06* | (2006.01) |
| *B01J 23/04* | (2006.01) |
| *B01J 23/883* | (2006.01) |
| *C10L 1/04* | (2006.01) |
| *B01J 21/08* | (2006.01) |
| *B01J 23/00* | (2006.01) |

(52) U.S. Cl.
CPC ............. *C07C 51/353* (2013.01); *B01J 21/04* (2013.01); *B01J 21/063* (2013.01); *B01J 23/04* (2013.01); *B01J 23/10* (2013.01); *B01J 23/30* (2013.01); *B01J 23/883* (2013.01); *B01J 35/002* (2013.01); *B01J 35/1014* (2013.01); *B01J 35/1019* (2013.01); *C07C 51/367* (2013.01); *C07C 59/347* (2013.01); *C07D 307/33* (2013.01); *C10G 3/46* (2013.01); *C10G 3/47* (2013.01); *C10G 3/48* (2013.01); *C10G 3/50* (2013.01); *C10G 50/00* (2013.01); *C10L 1/04* (2013.01); *C10L 1/06* (2013.01); *C10L 1/08* (2013.01); *B01J 21/08* (2013.01); *B01J 23/002* (2013.01); *B01J 35/10* (2013.01); *C10G 2300/202* (2013.01); *C10G 2300/301* (2013.01); *C10G 2300/302* (2013.01); *C10G 2300/304* (2013.01); *C10G 2400/02* (2013.01); *C10G 2400/04* (2013.01); *C10G 2400/08* (2013.01); *C10L 2200/0469* (2013.01); *C10L 2270/04* (2013.01); *Y02P 30/20* (2015.11)

(58) Field of Classification Search
CPC ... C07C 51/353; C07C 59/347; C07C 51/367; C10G 3/46; C10G 3/50; C10G 2300/202; C10G 2300/301; C10G 2300/302; C10G 2300/304; C10G 2400/02; C10G 2400/04; C10G 2400/08; C10G 3/47; C10G 3/48; C10G 50/00; B01J 21/04; B01J 21/063; B01J 21/08; B01J 23/002; B01J 23/04; B01J 23/10; B01J 23/30; B01J 23/883; B01J 35/002; B01J 35/10; B01J 35/1014; B01J 35/1019; C10L 1/04; C10L 1/06; C10L 1/08; C10L 2200/0469; C10L 2270/04
USPC .......................................................... 585/16
See application file for complete search history.

(56) References Cited

U.S. PATENT DOCUMENTS

| | | | |
|---|---|---|---|
| 2,440,751 A | 5/1948 | Legatski |
| 5,254,794 A | 10/1993 | Wu |

(Continued)

FOREIGN PATENT DOCUMENTS

| | | |
|---|---|---|
| CN | 102676201 A | 9/2012 |
| GB | 601922 A | 5/1948 |

(Continued)

OTHER PUBLICATIONS

Karimi, E. et. al.; "Ketonization and deoxygenation of alkanoic acids and conversion of levulinic acid to hydrocarbons using a Red Mud bauxite mining waste as the catalyst", Catalysis Today (2012), 190, pp. 73-88. (Year: 2012).*

(Continued)

*Primary Examiner* — Sharon Pregler
(74) *Attorney, Agent, or Firm* — Buchanan, Ingersoll & Rooney PC (57) ABSTRACT A method for the catalytic conversion of ketoacids, including methods for increasing the molecular weight of ketoacids, the method comprising the steps of providing in a reactor a feedstock comprising at least one ketoacid. The feedstock is then subjected to one or more C—C coupling reaction(s) in the presence of hydrogen, and in the presence of a catalyst system having both hydrogenation activity and C—C coupling activity.

18 Claims, 4 Drawing Sheets

(56) References Cited

U.S. PATENT DOCUMENTS

| | | | |
|---|---|---|---|
| 5,345,026 | A | 9/1994 | Chang et al. |
| 5,382,731 | A | 1/1995 | Chang et al. |
| 5,608,105 | A | 3/1997 | Fitzpatrick |
| 6,206,940 | B1 | 3/2001 | Weissman et al. |
| 8,003,818 | B2 | 8/2011 | Van Den Brink et al. |
| 8,362,306 | B2 | 1/2013 | Wheeler et al. |
| 8,629,310 | B2 | 1/2014 | Lotero et al. |
| 2006/0135793 | A1 | 6/2006 | Blessing et al. |
| 2006/0162239 | A1 | 7/2006 | Van Den Brink et al. |
| 2011/0098503 | A1 | 4/2011 | Wheeler et al. |
| 2012/0209037 | A1 | 8/2012 | Viljoen et al. |
| 2013/0079566 | A1 | 3/2013 | Lin |
| 2013/0237728 | A1* | 9/2013 | Lotero .................. C10L 1/04 585/242 |
| 2015/0018581 | A1 | 1/2015 | Kettunen et al. |
| 2015/0018588 | A1 | 1/2015 | Myllyoja et al. |

FOREIGN PATENT DOCUMENTS

| | | |
|---|---|---|
| GB | 762136 A | 11/1956 |
| WO | WO 95/03262 A1 | 2/1995 |
| WO | WO 00/47697 A1 | 8/2000 |
| WO | WO 2006/056591 A1 | 6/2006 |
| WO | WO 2006/067171 A1 | 6/2006 |
| WO | WO 2011/053584 A1 | 5/2011 |
| WO | WO 2013/113976 A1 | 8/2013 |
| WO | WO-2013113976 A1 * | 8/2013 .......... B01J 35/0006 |

OTHER PUBLICATIONS

Karimi, E. et. al. "Ketonization and deoxygenation of alkanoic acids and conversion of levulinic acid to hydrocarbons using a Red Mud bauxite mining waste as the catalyst", Catalysis Today, 190 (2012), pp. 73-88. (Year: 2012).*

International Search Report (PCT/ISA/210) dated Jul. 3, 2015, by the Finnish Patent Office as the International Searching Authority for International Application No. PCT/FI2015/050208.

International Search Report (PCT/ISA/210) dated Aug. 13, 2015, by the Finnish Patent Office as the International Searching Authority for International Application No. PCT/FI2015/050209.

International Search Report (PCT/ISA/210) dated Aug. 24, 2015, by the European Patent Office as the International Searching Authority for International Application No. PCT/EP2015/056655.

E. Karimi et al., "Ketonization and deoxygenation of alkanoic acids and conversion of levulinic acid to hydrocarbons using a Red Mud bauxite mining waste as the catalyst", Catalysis Today, 2012, pp. 73-88, vol. 190.

"World Jet Fuel Specifications with Avgas Supplement", ExxonMobil Aviation, 2005 Edition, XP055121730, Retrieved from the Internet: URL: http://www.exxonmobil.com/AviationsGlobal/Files/WorldJetFuelSpecifications2005.pdf [retrieved on Jun. 30, 2015].

Series 4555 Parr Floor Stand Reactors, 10-20 L. Internet Archive [online], [archived on Nov. 28, 2011], [retrieved on Jul. 2, 2015]. Retrieved from the Internet: <URL:https://web.archive.org/web/20111128224609/http://www.parrinst.com/products/stirred-reactors/series-4555-10-20-I-floor-stand-reactors/>.

* cited by examiner

Figure 1 – Conversion of lignocellulosic material to levulinic acid

Figure 2 – Reaction products of levulinic acid

Figure 3 – Process scheme for upgrading C-C coupling reactions

Figure 4 – Process scheme

METHOD FOR CATALYTIC CONVERSION OF KETOACIDS AND HYDROTREAMENT TO HYDROCARBONS

CROSS-REFERENCE TO RELATED APPLICATIONS

This application claims priority as a continuation application under 35 U.S.C. § 120 to PCT/FI2015/050208, which was filed as an International Application on Mar. 26, 2015 designating the U.S., and which claims priority to European Application 14161793.6 filed in Europe on Mar. 26, 2014. The entire contents of these applications are hereby incorporated by reference in their entireties.

FIELD

The present disclosure relates to catalytic conversion of ketoacids, including methods for increasing the molecular weight of ketoacids, reaction vessels suitable for such methods, C—C coupling reaction products obtainable by such methods, as well as use of such products for the production of liquid hydrocarbons and/or diesel fuel components.

BACKGROUND INFORMATION

Production of hydrocarbons used as fuel or heavy oil components and chemicals from biomass are of increasing interest since they are produced from a sustainable source of organic compounds.

Figure 1:
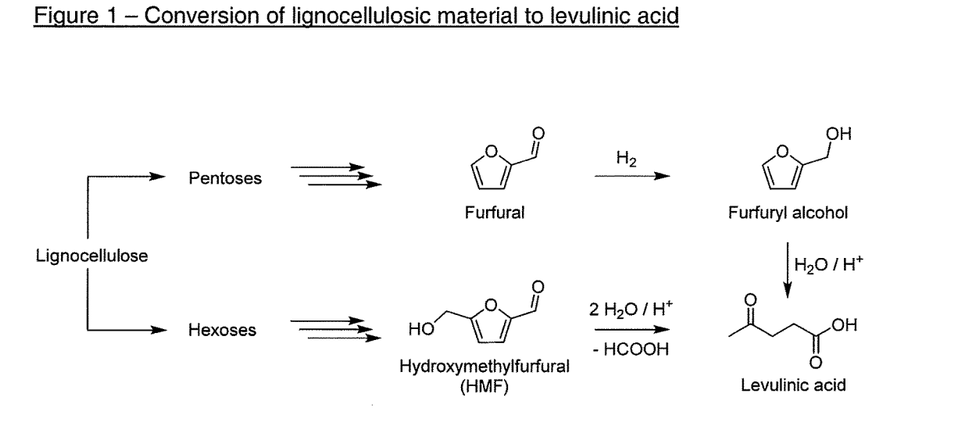
FIG. 1 shows a scheme illustrating conversion of lignocellulosic material to levulinic acid, according to an exemplary aspect.
Figure 2:
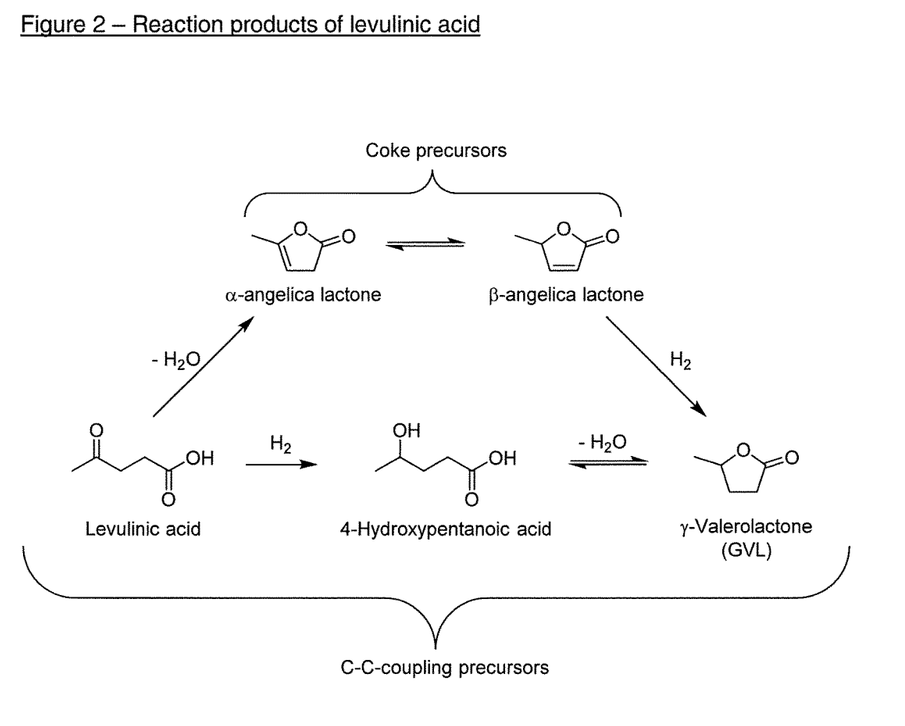
FIG. 2 shows a scheme illustrating some reaction products of levulinic acid, including potential coke precursors and potential C—C-coupling precursors, according to an exemplary aspect. The figure is not intended to cover all reaction products of levulinic acid, nor is it intended to show all types of coke precursors.

The ketoacid Levulinic acid (LA, 4-oxopentanoic acid) is one of many platform molecules that may be derived from biomass. It may be produced from both pentoses and hexoses of lignocellulosic material (see FIG. 1) at relatively low cost. Some of the advantages and drawbacks of using levulinic acid as a platform molecule relates to the fact that it is considered to be a reactive molecule due to both its keto and acid functionality.

Esters of levulinic acid have been suggested as fuel components as well as cold flow additives in diesel fuels, and in particular the methyl and ethyl esters have been used as additives in diesel fuel. Gamma-valerolactone (GVL), which may be obtained by reduction of levulinic acid, has been used as a fuel additive in gasoline. Further reduction of GVL to 2-methyltetrahydrofuran (MTHF) provides a product that may be blended with gasoline of up to 60%. Alkyl valerates produced from levulinic acid have also been suggested as biofuels.

Levulinic acid has also been used for the production of liquid hydrocarbon fuels by a number of catalytic routes, including a method of producing a distribution of alkenes, the distribution centered around $C_{12}$, involving converting aqueous GVL in a first reactor system to butenes followed by oligomerization in a second reactor over an acidic catalyst (for example, Amberlyst® 70).

Serrano-Ruiz et al. (*Appl. Catal., B,* 2010, 100, 184) produced a $C_9$-ketone (5-nonanone) by reducing levulinic acid to GVL over a Ru/C catalyst in one reactor followed by reacting 40 wt % GVL in water and 0.02 M $H_2SO_4$ in a Pd/$Nb_2O_5$+ceria-zirconia double bed arrangement at 325-425° C., 14 bar, WHSV=0.8-0.5 $h^{-1}$ in another reactor. Using multiple reactors may be advantageous as it can offer more control over the process compared to using a single reactor. However, multiple reactors increase the number of process steps, which is not desired.

US 2006/0135793 A1 (to Blessing and Petrus) discloses dimerization of levulinic acid to a $C_{10}$ unit in the presence of hydrogen, with a strong acidic heterogenous catalyst comprising a hydrogenating metal, at a temperature in the range from 60 to 170° C. and a pressure of 1 to 200 bar (absolute). The example indicates as main products levulinic acid dimers (26%) and unreacted levulinic acid (70%). Using a single reactor compared to multiple reactors may be advantageous in that it can reduce the number of process steps. Some of the drawbacks associated with direct routes of upgrading, for example, by using single reactors are that these reactions generate highly reactive intermediates with more than one functional group, which can further react to other (unwanted) molecules. Reduction of unwanted molecules by direct routes of upgrading in, for example, a single reactor usually entails a lower yield of the desired product composition. Accordingly, an indirect route of upgrading a feedstock using multiple reactors or multiple catalyst beds in a single reactor may in some situations be preferred compared to a direct route of upgrading.

Consequently, there is a need for additional processes for upgrading levulinic acid and other ketoacids to higher molecular weight compounds, which are suitable for use as, for example, fuel or heavy oil components or chemicals or as components in the production of fuel or heavy oil components or chemicals. For example, there is a need for such additional processes which reduce the processing costs by, for example, improving the yield of the desired components or chemicals and/or improving the life time of the catalyst.

SUMMARY

The present disclosure was made in view of the above. One exemplary aspect of the present disclosure is to provide methods that enable upgrading of ketoacids such as levulinic acid to higher molecular weight compounds.

Another exemplary aspect of the present disclosure is to provide the upgrade of ketoacids to higher molecular weight compounds in good yield and at low processing costs.

To address the problems discussed above, an exemplary aspect of the present disclosure provides a method for increasing the molecular weight of ketoacids, the method comprising the steps of providing in a reactor a feedstock comprising at least one ketoacid; and subjecting the feedstock to one or more C—C-coupling reaction(s); wherein the C—C-coupling reaction(s) are conducted in the presence of hydrogen; and in the presence of a dual function catalyst system having both hydrogenation activity and C—C-coupling activity.

That is, the inventors of the present disclosure in a first exemplary aspect of the disclosure found that the dual function catalyst both suppresses potential coking reactions of the reaction intermediates and simultaneously catalyzes multiple types of C—C-coupling reactions enabling the production of higher molecular weight compounds at a good yield and in a reactor.

In some exemplary embodiments, the C—C-coupling reaction(s) are conducted mainly in the liquid phase.

In some exemplary embodiments, the C—C-coupling reaction(s) are conducted in a single reactor.

In some exemplary embodiments, the feedstock is introduced into the reactor in liquid phase.

In some exemplary embodiments, the catalyst system is a mixture of one or more catalyst(s) having a hydrogenation activity and one or more catalyst(s) having a C C-coupling activity.

In some exemplary embodiments of the present disclosure, the feedstock being subjected to the one or more C—C-coupling reaction(s) has a water content of 15 wt % or less.

In some exemplary embodiments of the present disclosure, the catalyst system comprises a metal oxide catalyst having C—C-coupling activity. In some exemplary embodiments, the metal of the metal oxide catalyst is selected from the group consisting of oxides of one or more of the following metals: Na, Mg, K, Ca, Sc, Cr, Mn, Fe, Co, Ni, Cu, Zn, Sr, Ti, Y, Zr, Mo, Rh, Cd, Sn, La, Pb, Bi, Ti, V, and other rare earth metals.

In some exemplary embodiments of the present disclosure, the catalyst system comprises a noble metal catalyst and/or a transition metal catalyst having hydrogenation activity. In some exemplary embodiments, the noble metal catalyst and/or the transition metal catalyst is selected from a group consisting of: Fe, Pd, Pt, Ni, Mo, Co, Ru, Rh, W, or combinations thereof.

In some exemplary embodiments of the present disclosure, the catalyst system comprises $K_2O/TiO_2$ and $NiMo/Al_2O_3$.

In some exemplary embodiments of the present disclosure, the catalyst system contains 50-95% by weight, for example, 70-90% by weight of the metal oxide catalyst.

In some exemplary embodiments of the present disclosure, the catalyst system contains 5-50% by weight, for example, 10-30% by weight of the noble metal catalyst and/or the transition metal catalyst.

In some exemplary embodiments of the present disclosure, the catalyst system comprises 70-90% by weight of the metal oxide catalyst and 10-30% by weight of the noble metal catalyst and/or the transition metal catalyst; with the proviso that the catalyst system does not add up to more than 100%.

In some exemplary embodiments of the present disclosure, the C—C coupling reaction(s) are conducted at a temperature between 200-500° C., for example, between 240-400° C., for example, between 250-350° C.

In some exemplary embodiments of the present disclosure, the C—C coupling reaction(s) are conducted at a pressure of between 5-100 bar, for example, between 10-60 bar, for example, between 15-45 bar.

In some exemplary embodiments of the present disclosure, at least 60% of the feedstock comprises a ketoacid. In some exemplary embodiments of the present disclosure, the feedstock comprises levulinic acid.

In another exemplary aspect of the present disclosure, a C—C-coupling reaction product obtainable by the method according to the present disclosure is provided.

In another exemplary aspect of the present disclosure, a reactor for C—C coupling reaction(s) having a volume of more than 10 litres, comprising a catalyst system having both hydrogenation activity and C—C coupling activity, and a feedstock comprising a ketoacid is provided.

BRIEF DESCRIPTION OF THE DRAWINGS

Other exemplary features and exemplary advantages of the present disclosure will become apparent to those skilled in the art upon reading the detailed description of the embodiments in conjunction with the accompanying drawings, wherein:

FIG. 2 illustrates one possible mechanism for reducing the angelica lactone coke precursors by hydrogenation, and also illustrates that the intermolecular ester of 4-hydroxypentanoic acid, GVL, may be in equilibrium with 4-hydroxypentanoic acid itself.

DETAILED DESCRIPTION

In describing the exemplary embodiments of the disclosure, specific terminology will be resorted to for the sake of clarity. However, the disclosure is not intended to be limited to the specific terms so selected, and it is understood that each specific term includes all technical equivalents which operate in a similar manner to accomplish a similar purpose.

One of the challenges in increasing the molecular weight of ketoacids by C—C-coupling reactions is the high reactivity product intermediates, which result in too high degree of oligomerization of the starting components.

The inventors have found that the oligomerization of levulinic acid in gaseous phase in the presence of a typical ketonization catalyst results in high formation of coke and eventually plugging of the reactor. This is suggested to occur due to polymerization reactions, including reactions of levulinic acid to more reactive precursors such as angelica lactones, which are known to have a high tendency to polymerize under typical ketonization conditions.

It was attempted to reduce the unwanted polymerization reactions and control the ketonization reactions and coking by addition of steam to the reactor. The addition of water to suppress coking reactions was, however, found also to decrease the performance of the ketonization catalyst resulting in low yields of the condensation products.

An exemplary aspect of the disclosure is based on the finding that the molecular weight of ketoacids can be selectively increased by subjecting the ketoacids to C—C-coupling reactions in the presence of a dual function catalyst system, which suppresses the coking tendency of the reaction intermediates and simultaneously catalyzes multiple types of C—C-coupling reactions resulting in formation of new carbon-carbon bonds between the reactants.

Accordingly, in one exemplary aspect of the present disclosure, a method for increasing the molecular weight of ketoacids is provided, the method comprising the steps of providing in a reactor a feedstock comprising at least one ketoacid; and subjecting the feedstock to one or more C—C-coupling reaction(s); wherein the C—C-coupling reaction(s) are conducted in the presence of hydrogen; and in the presence of a catalyst system having both hydrogenation activity and C—C-coupling activity.

The present disclosure relates to a method for increasing the molecular weight of ketoacids and/or derivatives of ketoacids.

Ketoacids are organic molecules that have both a keto function ($>C=O$) as well as a carboxylic acid (COOH) or carboxylate ($COO^-$) function. According to an exemplary aspect, special forms of ketoacids include embodiments where the keto function is an aldehyde (CH=O), and in some embodiments the keto functionality may not be an aldehyde.

In some embodiments, the ketoacid is an alpha-ketoacid (such as pyruvic acid, oxaloacetic acid and alpha-ketoglutaric acid), beta-ketoacid (such as acetoacetic acid), gamma-ketoacid (such as levulinic acid), or delta-ketoacid. The ketoacid may have more than one keto functionality, and more than one carboxylic acid function. In some embodiments the ketoacid only has one keto functionality and one carboxylic acid functionality.

Scheme 1

Scheme 1 illustrates exemplary ketoacids according to the present disclosure, for example where n and m are integers each selected independently of each other from the list consisting of 0, 1, 2, 3, 4, 5, 6, 7, 8, 9, 10, for example, in exemplary embodiments where the ketoacid is levulinic acid (m=2, n=0).

In some embodiments, the ketoacid derivatives may be selected from gamma-valerolactone, angelica lactones and hydroxypentanoic acid.

The feedstock may comprise as the major component one or more ketoacids, for example, in some embodiments at least 30% such as at least 60%, at least 70%, at least 80%, at least 90%, at least 95% or 100% of the feedstock comprises a ketoacid or a derivative of a ketoacid. The feedstock may be obtained from processing of lignocellulosic material, and such processed material may be used directly, or purified to varying degrees before being used as a feedstock in the method of the present disclosure. In some embodiments, the feedstock comprises levulinic acid, and in some embodiments the levulinic acid may be combined with one or more other ketoacids. In other embodiments the feedstock comprises a mixture of levulinic acid in combination with gamma-valerolactone, such as at least 10% of levulinic acid and at least 10% of gamma-valerolactone.

In addition to ketoacids and ketoacid derivatives, the feedstock may also contain aldehydes, such as furfural or hydroxymethylfurfural.

In some embodiments of the present disclosure, the feedstock comprises levulinic acid.

The feedstock may contain water, and in some embodiments the feedstock has a water content of 15 wt % or less. In some embodiments, the water content is as low as possible, for example, a water content of 10 wt % or less, such as 5 wt % or less, or 1 wt % or less, for example, no water is present. In some embodiments, no external water is added during the C—C-coupling reaction(s), although internal water is produced in some condensation reactions.

In some embodiments, external water is added in an amount of 0.1 wt % to 10 wt % either to the feedstock and/or during the reactions, as, for example, steam.

In some embodiments, the feedstock is fed into in a single reactor, or single reactor bed. The reactor can be able to be pressurized, and to accommodate the feedstock and the catalyst system. The reactor can have means, such as one or more inlets and/or outlets, for supplying hydrogen and adding/withdrawing feedstock. Means for controlling the pressure and temperature can also be present.

The catalyst system may be provided as a mixture of two or more catalysts in the same bed in the reactor.

In some embodiments, the feedstock is introduced into the reactor in liquid phase, as opposed to for example the gaseous phase. An exemplary advantage of introducing the feedstock into the reactor in the liquid phase is that it is not required to heat the product to prepare a gaseous stream. In some embodiments, the C—C-coupling reaction(s) are conducted predominantly in the liquid phase, as opposed to the gaseous phase, meaning that the reaction is at least predominantly taking place on the catalyst in the liquid phase. In some embodiments, the C—C-coupling reaction(s) are conducted entirely in the liquid phase.

In some embodiments, the molecular weight of the ketoacids in the feedstock are increased at least 100% or more. In some embodiments, the molecular weight is increased to between 200 and 1500 g/mol, such as 200 and 500 g/mol. In some embodiments where the ketoacid is a $C_4$-$C_7$-ketoacid, the molecular weight is increased to corresponding molecules having a $C_{13}$-$C_{50}$ carbon chain, such as a $C_{13}$-$C_{30}$ carbon chain. For example, in some embodiments, more than 50 wt % of the reaction product may be determined to belong to the group containing trimerization, tetramerization, pentamerization, and hexamerization products. By trimerization, tetramerization, pentamerization and hexamerization products is meant reaction products relating to three, four, five and six molecules of one or more of ketoacids and derivatives thereof being coupled together. In the case of a feedstock comprising derivatives of ketoacids in addition to ketoacids, the trimerization, tetramerization, pentamerization, and hexamerization products may additionally contain mixed C—C-coupling products comprising one or more ketoacids and/or derivatives thereof. The trimerization, tetramerization, pentamerization, and hexamerization products are derived from at least one ketoacid, such as at least two ketoacids, at least three ketoacids, at least four ketoacid, at least five ketoacids, at least six ketoacids.

In the present disclosure, the molecular weight of the keto acids are increased through one or more C—C-coupling reaction(s). Many C—C-coupling reactions are known in the art, and the skilled person would be able to identify such C—C-coupling reactions based on the reaction conditions provided. For example, the C—C-coupling reactions may be ketonization reactions or reactions proceeding through an enol or enolate intermediate. In some embodiments, C—C-coupling reactions are selected from the list comprising: aldol-type reactions and condensations, ketonizations, reactions where the C—C-coupling involves an alkene, as well as other oligomerization reactions. The C—C-coupling reactions may proceed with two identical molecules or may be a crossed reaction between two different molecules.

For example, the C—C coupling reaction(s) proceeds in the presence of a catalyst system. It was found that subjecting the feedstock of the present disclosure to C—C-coupling reactions in the presence of a dual function catalyst, can suppress the coking tendency of the reaction intermediates and can simultaneously catalyze multiple types of C—C-coupling reactions resulting in formation of new carbon-carbon bonds between the reactants. The catalyst system can have both hydrogenation activity and C—C-coupling activity.

The inventors found that the problems related to the formation of coke during the C—C-coupling reactions of ketoacids such as levulinic acid and the low yield of the condensation products can be solved by using a dual function catalyst system comprising a first part having hydrogenation activity and a second part having C—C-coupling activity. Without wanting to be being bound to any theory, it is considered that the first part having hydrogenation activity inhibits the polymerization reactions of intermediates and the second part catalyzes the C—C coupling reactions responsible for increasing the molecular weight of the ketoacid.

In some embodiments, the catalyst system according to the present disclosure comprises at least two different catalysts, where one has predominantly hydrogenation activity, and the other predominantly C—C-coupling activity, and in other embodiments the catalyst system comprises a single catalyst having both hydrogenation activity and C—C-coupling activity. In some embodiments, the catalyst system is a mixture of one or more catalyst(s) having a hydrogenation activity and one or more catalyst(s) having a C—C-coupling activity, which for example may be prepared by mixing together one or more catalyst(s) having a hydrogenation activity with one or more catalyst(s) having a C—C-coupling activity (see, for example, the materials section of the examples). Additionally, the catalysts may be supported, such as, for example, on alumina, silica or active carbon support. Additionally, one or more of the catalysts may be sulfided. The catalysts may be prepared on a common support, or may be prepared on individual supports.

While both acids and bases may catalyse a number of C—C-coupling reactions, including the aldol reaction/condensation, such catalysts may be present in the feedstock, but are not intended to be comprised in the term catalyst system, in the context of the present disclosure. In some embodiments, the catalyst system is in the solid phase.

In some embodiments of the present disclosure, the catalyst system comprises a noble metal catalyst and/or a transition metal catalyst having hydrogenation activity. In some embodiments, the noble metal catalyst and/or the transition metal catalyst is selected from a group consisting of: Fe, Pd, Pt, Ni, Mo, Co, Ru, Rh, W, or combinations thereof.

In some embodiments of the present disclosure, the catalyst system contains 5-50% by weight, for example, 10-30% by weight of the noble metal catalyst and/or the transition metal catalyst.

In some embodiments of the present disclosure, the catalyst system comprises a metal oxide catalyst having C—C-coupling activity, and in some embodiments the metal of the metal oxide catalyst is selected from the group consisting of oxides of one or more of the following metals: Na, Mg, K, Ca, Sc, Cr, Mn, Fe, Co, Ni, Cu, Zn, Sr, Ti, Y, Zr, Mo, Rh, Cd, Sn, La, Pb, Bi, Ti, V, and other rare earth metals.

In some embodiments the metal of the metal oxide catalyst is K and/or Ti.

In some embodiments of the present disclosure, the catalyst system contains 50-95% by weight, for example, 70-90% by weight of the metal oxide catalyst.

In some embodiments of the present disclosure, the catalyst system comprises 70-90% by weight of the metal oxide catalyst and 10-30% by weight of the noble metal catalyst and/or the transition metal catalyst; with the proviso that the catalyst system does not add up to more than 100%.

In some embodiments of the present disclosure, the catalyst system comprises $K_2O/TiO_2$ and $NiMo/Al_2O_3$, such as 70-90% by weight of $K_2O/TiO_2$ (for example, 80 wt %) and 10-30% by weight of $NiMo/Al_2O_3$ (for example, 20 wt %).

The C—C coupling reaction(s) may proceed in the presence of hydrogen. The hydrogen may be mixed with one or more other gasses, for example, an inert gas such as helium or another of the noble gasses, or gas behaving inertly to the reaction conditions of the present disclosure. By behaving inertly is considered that the gas does not to a major extent participate as a reaction member, for example, the inert gas participates as little as possible, such as not participate at all.

The inventors found that the C—C coupling reaction(s) can be controlled by adjusting several parameters, including selection of a suitable ratio of the catalysts in the catalyst system, and by careful selection of reaction conditions such as: temperature, hydrogen-to-hydrocarbon ration (H:HC), pressure, weight hourly space velocity (WHSV) and time.

In some embodiments of the present disclosure, the C—C coupling reaction(s) are conducted at a temperature between 200-500° C., for example, between 240-400° C., for example, between 250-350° C.

In some embodiments the hydrogen-to-hydrocarbon ratio (H:HC) is from 100 to 600 Nl/l in the C—C coupling reactions, such as for example from 100 to 400 Nl/l, from 200 to 450 Nl/l, or from 200 to 400 Nl/l.

In some embodiments, the weight hourly space velocity (WHSV) is from 0.5 to 1.5 $h^{-1}$, such as 0.8 to 1.2 $h^{-1}$ in the C—C-coupling reactions.

In some embodiments of the present disclosure, the C—C coupling reaction(s) are conducted at a pressure of between 5-100 bar, for example, between 10-60 bar, for example, between 15-45 bar.

In another aspect of the present disclosure, a C—C-coupling reaction product obtainable by the method according to the present disclosure is provided. This product may be used as fuel or heavy oil components or chemicals or as intermediate components in production of fuel or heavy oil components or chemicals.

In another aspect of the present disclosure, a pressurizable vessel for C—C-coupling reaction(s) having a volume of at least 10 litres, comprising a catalyst system, which in one or more beds has a catalyst system, which is a mixture of catalyst(s) having both hydrogenation activity and C—C-coupling activity, a feedstock comprising a ketoacid and hydrogen is provided.

The C—C-coupling reaction product obtainable by the methods of the present disclosure may, if desired, be further subjected to a hydrodeoxygenation (HDO) step to remove oxygen, which in some embodiments produce completely deoxygenated material. The produced hydrocarbons may be used as fuel or heavy oil components or chemicals or as starting components in the production of fuel or heavy oil components or chemicals. The hydrodeoxygenated products may also be further isomerized to isoparaffins in the presence of hydrogen.

An exemplary advantage of the present disclosure is that ketoacids produced from renewable materials can be upgraded to higher molecular weight compounds, which may be used as fuel or heavy oil components or chemicals or as starting components in the production of fuel or heavy oil components or chemicals.

Figure 3:
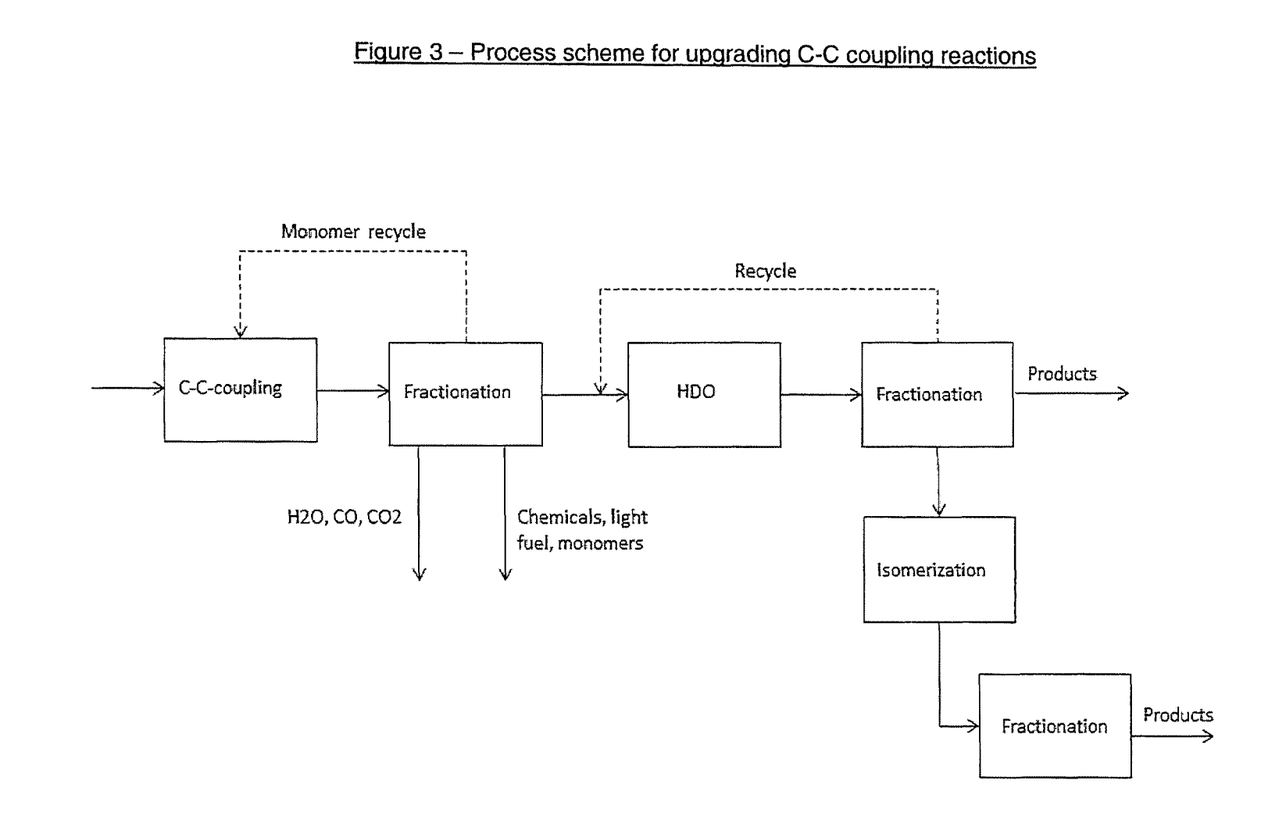
FIG. 3 shows an overview of a possible process scheme for further upgrading the products from the C—C-coupling reactions, according to an exemplary aspect.
Figure 4:
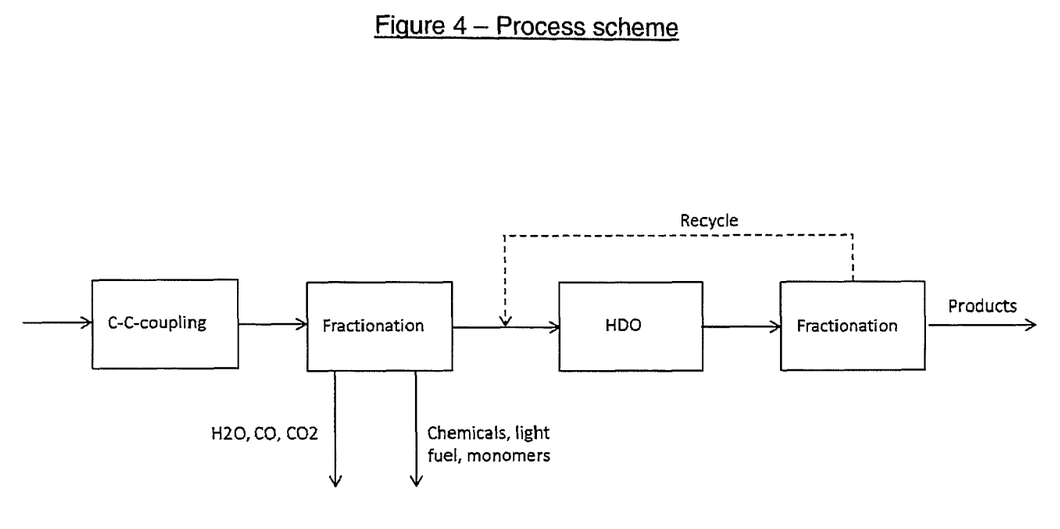
FIG. 4 shows an overview of a possible process scheme for preparing and upgrading the products from the C—C-coupling reactions, according to an exemplary aspect.

The C—C-coupling reaction products may be fractionated to remove potential unreacted ketoacid monomers and other light components such as water and $CO_2$ formed in the C—C-coupling reactions from the reaction product as illustrated in FIG. 3. The fractionation can be conducted by any suitable means such as distillation. The unreacted ketoacid monomer may optionally be recycled and combined with the feed of the first reactor.

Accordingly, in another aspect of the present disclosure, a method for production of hydrocarbons is provided, the method comprising subjecting the C—C-coupling reaction products obtained to a hydrodeoxygenation step in the presence of a hydrodeoxygenation (HDO) catalyst. In some embodiments, the HDO catalyst comprises a hydrogenation metal on a support, such as for example a HDO catalyst selected from a group consisting of Pd, Pt, Ni, Co, or any combination of these. The hydrodeoxygenation step may, for example, be conducted at a temperature of 100-500° C. and at a pressure of 10-150 bar.

In another aspect of the present disclosure, a kerosene product composition is provided comprising a mixture of C—C-coupling products of levulinic acid, having a boiling point range (10% and 90% fraction as determined by ASTMD2887) from 170° C. to 300° C.; a carbon and a hydrogen content (as determined by ASTMD5291) of more than 80 wt % and more than 10%, respectively; where an aromatic content (as determined by ASTMD6379) is between 10-20 vol %; where a sulphur content (as determined by ASTMD7039) is lower than 7 ppmw, preferably lower than 3 ppmw.

In some embodiments, the kerosene product composition additionally has one or more characteristics selected from one or more of the list consisting of: a cloud point (as determined by ASTMD7689) lower than −90° C.; a heat value (as determined by ASTMD3338) of more than 40 MJ/kg; a density (as determined by ENISO12185) is between 830-850 kg/m$^3$ at 15° C. and between 805-835 kg/m$^3$ at 50° C.; and a viscosity between 9-11 mm$^2$/s at −20° C.

Water and light gases may be separated from the HDO product with any conventional means such as distillation. After the removal of water and light gases, the HDO product may be fractionated to one or more fractions suitable for use as gasoline, aviation fuel, diesel or heavy oil components. The fractionation may be conducted by any suitable means, such as distillation. Optionally, part of the product of the HDO step may be recycled and combined to the feed of the HDO reactor.

The product of the hydrodeoxygenation step may also be subjected to an isomerization step in the presence of an isomerization catalyst and hydrogen. Both the hydrodeoxygenation step and isomerisation step may be conducted in the same reactor. In some embodiments, the isomerisation catalyst is a noble metal bifunctional catalyst, for example Pt-SAPO or Pt-ZSM-catalyst. The isomerization step may, for example, be conducted at a temperature of 200-400° C. and at a pressure of 20-150 bar.

It is exemplary that only a part of the HDO product is subjected to an isomerization step, for example, the part of HDO product which is subjected to isomerization may be the heavy oil fraction boiling at or above temperature of 300° C.

The hydrocarbon product obtainable from the hydrodeoxygenation and/or the isomerisation step may be used as fuel or heavy oil components or chemicals or as intermediate components in production of fuel or heavy oil components or chemicals.

For example, the choice of subjecting HDO product to isomeration is highly dependable of the desired properties of the end products. For example, aromatic compounds are desirable if the end product is aviation fuel since the Jet fuel standard may require a certain amount of aromatic compounds to be present in aviation fuel. For example, since the isomerization is known to decompose aromatic and cyclized compounds, the HDO product would not necessarily be subjected to isomerization step if the object is to produce aviation fuel. On the other hand, it can be advantageous to minimize the amount of aromatic compounds in diesel fuel since the aromatics decrease the cetane number of diesel.

When describing the embodiments of the present disclosure, the combinations and permutations of all possible embodiments have not been explicitly described. Nevertheless, the mere fact that certain measures are recited in mutually different dependent claims or described in different embodiments does not indicate that a combination of these measures cannot be used to advantage. The present disclosure envisages all possible combinations and permutations of the described embodiments.

The terms "comprising", "comprise" and comprises herein are intended by the inventors to be optionally substitutable with the terms "consisting of", "consist of" and "consists of", respectively, in every instance.

EXAMPLES

The examples show that it is possible to increase the molecular weight of levulinic acid by C—C-coupling reactions conducted in the presence of hydrogen and a dual function catalyst system comprising a metal oxide catalyst and a hydrotreatment catalyst. The examples also show that the C—C-coupling reaction product of levulinic acid can be further processed to hydrocarbons having a boiling point range of typical fuel or heavy oil components such as naphta, kerosene and diesel and heavy oil components by subjecting the C—C-coupling reaction product of levulinic acid to hydrodeoxygenation reactions in the presence of a typical HDO catalyst and hydrogen.

The examples also show that the hydrocarbon products having a boiling point range of typical fuel or heavy oil components such as naphta, kerosene and diesel produced in the experiments have excellent cold properties without further isomerization treatment.

Materials

Preparation of 80/20 wt % $K_2O/TiO_2$—$NiMo/Al_2O_3$ Catalyst System

As a hydrogenation catalyst, a pre-sulfided $NiMo/Al_2O_3$ catalyst (obtained from Albemarle) with the composition given in table 1 was used.

As a C—C coupling catalyst, a $K_2O/TiO_2$ catalyst (obtained from BASF) with the composition given in table 1 was used.

The $K_2O/TiO_2$—$NiMo/Al_2O_3$ catalyst system was prepared by crushing both catalysts, sieving them to a particle size of 0.15-0.35 mm before thoroughly mixing the two together to prepare the catalyst system.

TABLE 1

Composition of $K_2O/TiO_2$ and $NiMo/Al_2O_3$ catalyst

| $K_2O/TiO_2$ catalyst | | $NiMo/Al_2O_3$ catalyst | |
|---|---|---|---|
| | Amount, % | | Amount, % |
| $TiO_2$ | 96.7 | NiO | 3.4 |
| $SiO_2$ | 0.0 | $MoO_3$ | 13.2 |
| $MnO_2$ | 0.0 | $K_2O$ | 0 |
| $K_2O$ | 2.4 | Al | 44 |
| $Nb_2O$ | 0.1 | Mo | 8.7 |
| CaO | 0.0 | Ni | 2.6 |
| FeO | 0.0 | Fe | 0.0 |
| MgO | 0.0 | Na | 0.0 |
| $CeO_3$ | 0.3 | | |

Example 1

Increasing the Molecular Weight of Levulinic Acid by C—C Coupling Reactions

Levulic acid with a purity of >99.9% was introduced in a trickle bed reactor to C—C coupling reactions in the presence of the 80/20 wt % $K_2O/TiO_2$—$NiMo/Al_2O_3$ catalyst system prepared above.

The C—C coupling reactions were conducted at temperature ranging from about 250 to about 350° C. and under a pressure of about 20 bar to 40 bar, using a hydrogen to hydrocarbon ($H_2$/HC) ratio of about 200 to 400 Nl/l and weight hourly space velocity (WHSV) of about 1.0 $h^{-1}$. WHSV and hydrogen to hydrocarbon ratio was calculated from the amount of levulic acid fed in vessel.

The complete catalytic reaction was conducted with the same catalyst over the course of 5 weeks. Each experiment (EX 1-12) was performed over a period of 2-5 days.

The process conditions and yields are presented in Table 2. Oil product distributions are presented in Table 3. Oil product distribution was obtained by gel permeation chromatography using refractive index as the detector and tetrahydrofuran as eluent. A peak is present where levulinic acid eluted. Elution times after levulinic acid was ascribed to monomers, i.e., non-C—C-coupled products, which could be smaller molecular weight compounds compared to levulinic acid. For products eluting earlier than the levulinic acid, two peaks could be seen, one which could be ascribed to dimers of levulinic acid based on GC-MS, and a broader peak, which could be ascribed to oligomers derived from three or more molecules of levulinic acid. The Monomer, Levulinic acid, Dimer and Oligomer columns in table 3 are based on the area under the peaks in the GPC chromatogram.

TABLE 2

Process conditions and process yields.

| Process conditions | | | | Process yields | | | |
|---|---|---|---|---|---|---|---|
| Temperature ° C. | Pressure bar | H:HC liter/liter | WHSV $h^{-1}$ | $H_2O$ yield % | Gas yield % | Oil yield % | Experiment |
| 251 | 19 | 210 | 1 | 0 | 12 | 88 | EX 1 |
| 274 | 21 | 215 | 1 | 0 | 9 | 91 | EX 2 |
| 299 | 20 | 231 | 1 | 0 | 20 | 80 | EX 3 |
| 299 | 21 | 426 | 1 | 0 | 12 | 88 | EX 4 |
| 299 | 42 | 390 | 1 | 10 | 16 | 74 | EX 5 |
| 326 | 41 | 391 | 1 | 15 | 22 | 64 | EX 6 |
| 350 | 40 | 400 | 1 | 21 | 24 | 55 | EX 7 |
| 349 | 40 | 213 | 1 | 20 | 27 | 53 | EX 8 |
| 349 | 22 | 205 | 1 | 24 | 26 | 50 | EX 9 |
| 324 | 21 | 204 | 1 | 18 | 25 | 57 | EX 10 |
| 324 | 41 | 214 | 1 | 17 | 24 | 59 | EX 11 |
| 298 | 19 | 209 | 1 | 0 | 17 | 83 | EX 12 |

TABLE 3

Oil product distributions.

| Oil composition | | | | |
|---|---|---|---|---|
| Monomer area-% | Levulic acid area-% | Dimer area-% | Oligomer area-% | Experiment |
| 12 | 48 | 30 | 11 | EX 1 |
| 10 | 38 | 28 | 24 | EX 2 |
| 5 | 10 | 16 | 70 | EX 3 |
| 7 | 12 | 18 | 63 | EX 4 |
| 13 | 17 | 27 | 43 | EX 5 |
| 14 | 5 | 34 | 47 | EX 6 |
| 6 | 17 | 21 | 56 | EX 7 |
| 4 | 11 | 18 | 68 | EX 8 |
| 3 | 10 | 16 | 72 | EX 9 |
| 3 | 8 | 16 | 74 | EX 10 |
| 6 | 9 | 21 | 65 | EX 11 |
| 3 | 12 | 18 | 68 | EX 12 |

The products obtained from experiments 1 to 12 were fractionated in a distillation apparatus. Each sample was fractionated with cut point of 200° C. Water obtained in distillate was separated with a tap funnel. Yields from the fractional destillation are presented in Table 4.

TABLE 4

Oil product fractions from experiments 1-12.

| $H_2O$ % | <200° C. % | >200° C. % | Experiment |
|---|---|---|---|
| 11 | 1 | 88 | EX 1 |
| 16 | 2 | 82 | EX 2 |
| 25 | 2 | 74 | EX 3 |
| 24 | 2 | 74 | EX 4 |
| 17 | 3 | 79 | EX 5 |
| 13 | 13 | 74 | EX 6 |
| 20 | 8 | 72 | EX 7 |
| 9 | 9 | 82 | EX 8 |
| 10 | 6 | 84 | EX 9 |
| 13 | 5 | 82 | EX 10 |
| 13 | 6 | 81 | EX 11 |
| 19 | 2 | 79 | EX 12 |

Example 2

Hydrodeoxygenation of the C—C Coupling Reaction Product Fractions

This example uses the higher boiling fractions (>200° C.) in table 4, which were subjected to hydrodeoxygenation step to remove heteroatoms and to stabilize the oil product.

The fractionated oil product (>200° C.) from Experiment 5 of Example 1 represented a HDO oil product feed with moderate conversion (C—C-coupling reactions conducted at a temperature of 300° C.).

The fractionated oil products (>200° C.) from Experiments 1 and 2 of Example 1 were pooled to represent a HDO oil product feed with low conversion (C—C-coupling reactions conducted at temperatures of 250-275° C.).

The fractionated oil products (>200° C.) from Experiments 7, 8 and 9 of Example 1 were pooled to represent a HDO oil product feed with moderately high conversion (C—C coupling reactions conducted at a temperature of 325° C.).

The fractionated oil products (>200° C.) from Experiments 6, 10 and 11 of Example 1 were pooled to represent a HDO oil product feed with high conversion (C—C coupling reactions conducted at a temperature of 350° C.).

These four oil product fractions described above were subjected to hydrodeoxygenating reactions (HDO) to remove heteroatoms and to stabilize oil product. Hydrodeoxygenation was carried out in presence sulfided NiMo on alumina carrier catalyst at temperature of 310° C. and under a pressure of 50 bar using hydrogen to hydrocarbon ($H_2$/HC) ratio of 3000 Nl/l and weight hourly space velocity (WHSV) of 0.3 h$^{-1}$. WHSV and hydrogen to hydrocarbon ratio is calculated from the amount of tested oil fed in vessel. Process conditions and process yields are presented in Table 5, and the HDO oil product distribution is presented in Table 6. The HDO oil product boiling point distribution was obtained by GC-distillation (ASTMD 2887).

TABLE 5

HDO process conditions and process yields.

| Temperature ° C. | Pressure bar | H:HC liter/liter | WHSV h$^{-1}$ | $H_2O$ yield % | Gas yield % | Oil yield % | Experiment |
|---|---|---|---|---|---|---|---|
| 308 | 53 | 3061 | 0.3 | 16 | 39 | 45 | EX 13 |
| 309 | 55 | 2770 | 0.3 | 27 | 39 | 34 | EX 14 |
| 307 | 53 | 3353 | 0.3 | 9 | 28 | 64 | EX 15 |
| 309 | 52 | 3220 | 0.3 | 8 | 26 | 66 | EX 16 |

TABLE 6

HDO Oil product boiling point distribution.

| Bp: <180° C. | Bp: 180-360° C. | Bp: >360° C. | Experiment |
|---|---|---|---|
| 22% | 53% | 25% | EX 13 |
| 27% | 48% | 25% | EX 14 |
| 13% | 51% | 36% | EX 15 |
| 13% | 44% | 44% | EX 16 |

Example 3

Physical Properties of Hydrodeoxygenated C—C Coupling Reaction Products

The HDO oil product of Experiment 13 of Example 2 was distilled in reduced pressure to fuel and heavy oil fractions, and some of the properties measured. Properties of the distilled fractions are shown in Table 7. The properties of the kerosene product in table 7 makes it suitable for a use as a Jet fuel.

TABLE 7

Properties of distilled HDO product fractions of Experiment 13.

| | | | Naphta/kerosene | Kerosene | Diesel | Diesel | Heavy oil |
|---|---|---|---|---|---|---|---|
| ENISO12185 | Density 15° C. | kg/m$^3$ | 784.2 | 845.1 | 898.6 | 865.6 | |
| ENISO12185 | Density 50° C. | kg/m$^3$ | 753.0 | 820 | 875 | 841.4 | |
| ASTMD7689 | Cloud point | ° C. | | Below −95 | Below −95 | Below −95 | |
| ASTMD7346 M | Pour point | ° C. | | | | | |
| ENISO3104 | Viscosity −20° C. | mm$^2$/s | | | 9.809 | | |
| ENISO3104 | Viscosity 80° C. | mm$^2$/s | | | | | |
| ENISO3104 | Viscosity 100° C. | mm$^2$/s | | | | | |
| ASTMD7039 | Sulfur | mg/kg | | 1 | 5 | | |
| ASTMD6379 | Aromates | vol-% | | 14.3 | | | |
| ASTMD5291 | Carbon | wt-% | | 85.9 | | | |
| ASTMD5291 | Hydrogen | wt-% | | 13.4 | | | |
| ASTMD3338 | Heat value | MJ/kg | | 45.746 | | | |
| ASTMD2887 | Bp ° C. | 10% | 141 | 170 | 285 | 188 | 378 |
| ASTMD2887 | Bp ° C. | 20% | 146 | 200 | 298 | 220 | 405 |
| ASTMD2887 | Bp ° C. | 30% | 149 | 218 | 306 | 237 | 427 |
| ASTMD2887 | Bp ° C. | 40% | 149 | 229 | 314 | 251 | 450 |
| ASTMD2887 | Bp ° C. | 50% | 150 | 240 | 321 | 270 | 474 |
| ASTMD2887 | Bp ° C. | 60% | 153 | 248 | 329 | 292 | 500 |
| ASTMD2887 | Bp ° C. | 70% | 162 | 259 | 338 | 312 | 529 |
| ASTMD2887 | Bp ° C. | 80% | 170 | 275 | 349 | 333 | 564 |
| ASTMD2887 | Bp ° C. | 90% | 187 | 297 | 366 | 364 | 614 |

It will therefore be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. A method for increasing the molecular weight of ketoacids, the method comprising:
    a) providing in a reactor a feedstock having at least one ketoacid; and
    b) subjecting the feedstock to one or more C—C coupling reaction(s),
    wherein the C—C coupling reaction(s) are conducted in a presence of hydrogen, and wherein the C—C coupling reaction(s) are conducted in a presence of a catalyst system having both hydrogenation activity and C—C coupling activity at a temperature between 200-500° C. and at a pressure of between 5-150 bar, and wherein the catalyst system includes 70-90% by weight of a metal oxide catalyst and 10-30% by weight of a noble metal catalyst and/or a transition metal catalyst, and wherein the catalyst system is in a same bed in the reactor.

2. The method according to claim 1, wherein the feedstock is introduced into the reactor in liquid phase.

3. The method according to claim 1, wherein the C—C coupling reaction(s) are conducted in a single reactor.

4. The method according to claim 1, wherein the catalyst system is a mixture of one or more catalyst(s) having hydrogenation activity and one or more catalyst(s) having C—C coupling activity.

5. The method according to claim 1, wherein the feedstock being subjected to the one or more C—C coupling reaction(s) has a watercontent of 15 wt % or less.

6. The method according to claim 1, wherein the catalyst system comprises a metal oxide catalyst having C—C coupling activity, and wherein the metal of the metal oxide catalyst comprises at least one or more of the following metals: Na, Mg, K, Ca, Sc, Cr, Mn, Fe, Co, Ni, Cu, Zn, Sr, Ti, Y, Zr, Mo, Rh, Cd, Sn, La, Pb, Bi, Ti, V, or a rare earth metal.

7. The method according to claim 1, wherein the catalyst system comprises a noble metal catalyst and/or a transition metal catalyst having hydrogenation activity and wherein the noble metal catalyst and/or the transition metal catalyst is selected from the group consisting of: Fe, Pd, Pt, Ni, Mo, Co, Ru, Rh, W, and a combination thereof.

8. The method according to claim 1, wherein the catalyst system comprises $K_2O/TiO_2$ and $NiMo/Al_2O_3$.

9. The method according to claim 1, wherein the C—C coupling reaction(s) are conducted at a temperature between 240-400° C.

10. The method according to claim 1, wherein the C—C coupling reaction(s) are conducted at a pressure of between 10-60 bar.

11. The method according to claim 1, wherein the feedstock comprises levulinic acid.

12. The method according to claim 1, wherein at least 60 wt-% of the feedstock comprises a ketoacid.

13. The method according to claim 1, wherein the C—C coupling reaction(s) are conducted at a hydrogen-to-feedstock ratio from 100 to 600 Nl/l.

14. A C—C coupling reaction product obtained by the method of claim 1.

15. The method according to claim 1, wherein the C—C coupling reaction(s) are conducted at a temperature between 250-350° C.

16. The method according to claim 1, wherein the C—C coupling reaction(s) are conducted at a pressure of between 15-45 bar.

17. The method according to claim 2, wherein the C—C coupling reaction(s) are conducted in a single reactor.

18. The method according to claim 2, wherein the catalyst system is a mixture of one or more catalyst(s) having hydrogenation activity and one or more catalyst(s) having C—C coupling activity.

* * * * *